(12) United States Patent
Kaneko et al.

(10) Patent No.: US 6,316,558 B1
(45) Date of Patent: Nov. 13, 2001

(54) TRANSITION METAL COMPOUND, OLEFIN POLYMERIZATION CATALYST COMPRISING THE COMPOUND, AND PROCESS FOR PRODUCTION OF OLEFIN POLYMER

(75) Inventors: Toshiyuki Kaneko; Ryuji Ikeda; Akihiro Yano; Morihiko Sato, all of Mie (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/039,495

(22) Filed: Mar. 16, 1998

Related U.S. Application Data (62) Division of application No. 08/788,761, filed on Jan. 24, 1997, now abandoned.

(30) Foreign Application Priority Data

Jan. 25, 1996 (JP) .................................................. 8-10803

(51) Int. Cl.[7] .............................. C08F 4/52; C08F 4/642
(52) U.S. Cl. .......................... 526/133; 526/134; 526/160; 526/943; 526/124.3; 526/129; 502/117; 502/118
(58) Field of Search ..................... 526/160, 943, 526/133, 134

(56) References Cited

U.S. PATENT DOCUMENTS

| | | | |
|---|---|---|---|
| 4,892,851 | 1/1990 | Ewen et al. | 502/117 |
| 5,036,034 | 7/1991 | Ewen | 502/117 |
| 5,155,080 | 10/1992 | Elder et al. | 502/117 |
| 5,308,811 | 5/1994 | Suga et al. | 502/103 |
| 5,308,817 | 5/1994 | Reddy et al. | 502/103 |
| 5,387,568 | 2/1995 | Ewen et al. | 502/103 |
| 5,416,228 * | 5/1995 | Ewen et al. | 556/7 |
| 5,434,115 * | 7/1995 | Yamada et al. | 502/103 |
| 5,455,214 | 10/1995 | Furtek et al. | 502/103 |
| 5,500,398 | 3/1996 | Marks et al. | 502/103 |
| 5,502,017 | 3/1996 | Marks et al. | 502/103 |
| 5,504,049 | 4/1996 | Crowther et al. | 502/103 |
| 5,525,690 | 6/1996 | Chiari et al. | 502/103 |
| 5,534,473 * | 7/1996 | Welch et al. | 502/117 |
| 5,561,092 * | 10/1996 | Ewen et al. | 502/117 |
| 5,571,880 | 11/1996 | Alt et al. | 502/117 |
| 5,650,471 * | 7/1997 | Abe et al. | 526/160 |
| 6,121,396 * | 9/2000 | Sone et al. | 526/153 |

FOREIGN PATENT DOCUMENTS

| | | |
|---|---|---|
| 0503422 | 3/1992 | (EP) . |
| 503422 * | 9/1992 | (EP) . |
| 0610847 | 2/1994 | (EP) . |
| 0747406 | 6/1996 | (EP) . |
| 6122718 | 6/1994 | (JP) . |

OTHER PUBLICATIONS

Journal of Organometallic Chemistry, vol. 514, No. 1996, May 17, 1996, pp. 257–270, H.G. Alt et al., Syndiospezifische Polymerisation von Propylen: . . . ( . . . Me, Ph).

* cited by examiner

*Primary Examiner*—David W. Wu
*Assistant Examiner*—R. Rabago
(74) *Attorney, Agent, or Firm*—Sughrue, Mion, Zinn, Macpeak & Seas, PLLC (57) ABSTRACT

A polyolefin of a high molecular weight is produced by using a catalyst comprising a transition metal compound represented by General Formula (1):

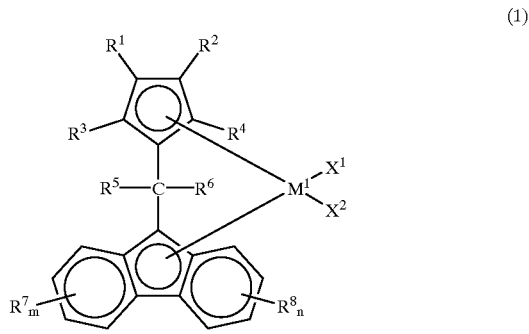

4 Claims, 5 Drawing Sheets

TRANSITION METAL COMPOUND, OLEFIN POLYMERIZATION CATALYST COMPRISING THE COMPOUND, AND PROCESS FOR PRODUCTION OF OLEFIN POLYMER

This is a divisional of application Ser. No. 08/788,761 filed Jan. 24, 1997 abandoned.

BACKGROUND OF THE INVENTION

1. Field of the Invention

The present invention relates to a transition metal compound having a substituted cyclopentadienyl group as a ligand and a fluorenyl group as another ligand, both ligands being bridged by a diarylmethylene group. The present invention relates also to a process for producing the transition metal compound. The present invention further relates to an olefin polymerization catalyst employing the transition metal compound. The present invention further relates to a process for producing an olefin polymer using the catalyst.

2. Description of the Related Art

For olefin polymerization, a metallocene catalyst is known which comprises a cyclopentadienyl derivative of a transition metal such as titanium, zirconium, and hafnium (metal of Group 4 of the Periodic Table) and an aluminoxane as basic constituents, as shown in publications such as J.Boor: "Ziegler-Natta Catalyst and Polymerization", Academic Press, New York (1979); and H.Sinn and W.Kaminsky: Adv. Organomet. Chem., 1899 (1980).

In α-olefin polymerization, it is known that a substituent in the cyclopentadienyl ring ligand, or the bridge between the two cyclopentadienyl ring ligands of the metallocene compound, affects greatly the stereotacticity and molecular weight of the resulting a-olefin polymer. For example, isotactic polypropylene was obtained by use, as the catalyst, of a racemic complex of a transition metal of Group 4 having an ethylenebis(indenyl) ligand in which two indenyl rings are linked by an ethylene bridge, as shown in J. Am. Chem. Soc., 106, 6355, (1984); Angew. Chem. Int. Ed. Engl., 24, 507, (1985); and J. Am. Chem. Soc., 109, 6544 (1987). Syndiotactic polypropylene was obtained by use, as the catalyst, of a transition metal complex of Group 4 having an isopropylidene(cyclopentadienyl) (9-fluorene) ligand constituted of a cyclopentadiene group and a fluorene group bridged by isopropylidene.

Syndiotactic polypropylene was obtained by use, as the propylene polymerization catalyst, of diphenylmethylene (cyclopentadienyl) (fluorenyl) zirconium dichloride which was derived by replacing the dimethylmethylene group of the above transition metal complex of Group 4 having an isopropylidene-(cyclopentadienyl) (9-fluorene) ligand by a diphenylmethylene group, as shown in JP-A-2-274703.

The stereotacticity of poly-α-olefins is known to be varied over a wide range from atactic to isotactic by use of a transition metal complex containing an isopropylidene (cyclopentadienyl)(9-fluorene) ligand substituted at the 3-position of the cyclopentadiene ring by an alkyl group such as methyl and t-butyl and by changing the kind and number of the substituents. For example, hemiisotactic polypropylene was obtained by use of isopropylidene(3-methylcyclopentadienyl)(fluorenyl)-zirconium dichloride having a methyl group as the substituent at the 3-position of the cyclopentadienyl ring, as shown in Makromol. Chem., Macromol. Symp., 48–49, 235 (1991); and JP-A-3-193796. Isotactic polypropylene was obtained by use of isopropylidene(3-t-butylcyclopentadienyl)(fluorenyl) zirconium dichloride which has similarly a t-butyl group at the 3-position of the cyclopentadienyl group, as shown in JP-A-6-122718.

On the other hand, the transition metal compound having a cyclopentadienyl group substituted at 3-position, a fluorenyl group, and a diphenylmethylene bridge between the cyclopentadienyl group and the fluorenyl group could not efficiently be synthesized. Generally, isopropylidene-(cyclopentadienyl)(9-fluorene) as a ligand is synthesized by reaction of a metal salt of fluorene with 6,6-dimethylfulrene, and a ligand having a substituted cyclopentadienyl group is synthesized in a similar manner. However, the ligand of the above compound cannot readily be synthesized since the reaction does not proceed rapidly between the metal salt of fluorene and the 6,6-dimethylfulrene derivative substituted at the five-membered ring moiety by an electron-donating hydrocarbon substituent.

In polymerization of an α-olefin, metallocene catalysts generally do not give high molecular weight poly-α-olefins. For example, syndiotactic, hemitactic, or isotactic polypropylene is obtained, respectively, by use of a catalyst comprising a transition metal compound having a ligand composed of a cyclopentadiene derivative, fluorene, and a dimethylmethylene bridge therebetween, specifically the aforementioned isopropylidene(cyclopentadienyl) (fluorenyl)-zirconium dichloride, isopropylidene(3-methylcyclo-pentadienyl)(fluorenyl)zirconium dichloride, or isopropylidene(3-t-butylcyclopentadienyl)(fluorenyl)-zirconium dichloride, but the molecular weight of the polymer is low.

In copolymerization of ethylene with an α-olefin, metallocene catalysts produce copolymers of uniform composition distribution differently from conventional Ziegler-Natta catalysts. Various olefin copolymers ranging from linear low-density polyethylene (LLDPE) to an ethylene-propylene copolymer (EPR) can be produced by use of the metallocene catalyst. However, the metallocene catalyst involve s a problem that the molecular weight of the polymer produced at a higher polymerization temperature is significantly lower. JP-A-5-320246 discloses copolymerization of ethylene with 1-octene at a high temperature by use of a cationic transition metal catalyst prepared from dicyclopentadienyl zirconium dichloride, dimethylanilinium tetraphenylborate, and triisobutylaluminum. However, the produced polymer had a low intrinsic viscosity, and a low molecular weight .

In synthesis of olefin type elastomers typified by EPR, the metallocene catalyst involves problems in molecular weight and productivity. Generally, with the metallocene catalyst, the molecular weight of the produced polymer becomes remarkably lower with increase of the amount of α-olefin. JP-A-62-121709 and JP-A-121711 disclose synthesis examples of low crystalline ethylene/α-olefin copolymers, and ethylene/α-olefin/nonconjugated dienes by use of a catalyst prepared from bis(cyclopentadienyl)zirconium monochloride monohydride and methylaluminoxane, in which the polymerization was conducted at a low temperature in order to obtain the desired high molecular weight, but the yield of the polymer was low and the productivity was disadvantageously low. JP-A-5-43618 discloses a production example of EPR by use of a cationic transition metal catalyst prepared from ethylenebis(indenyl)dimethyl-zirconium, ferrocenium tetrakis(pentafluorophenyl)borate, and triisobutylaluminum, but the problem of the molecular weight is not solved.

SUMMARY OF THE INVENTION

The present invention intends to provide a highly active catalyst system for producing a polyolefin of a high molecular weight by a conventional technique under industrial polymerization conditions without the aforementioned problems.

The present invention also intends to provide a novel transition metal compound therefor, and an efficient process for preparing the transition metal compound.

After comprehensive investigation, it was found that a polyolefin of a high molecular weight can be produced with high productivity by use of a catalyst comprising, as a component, a transition metal compound having a ligand composed of a compound in which a substituted cyclopentadienyl and fluorene are linked together by a diarylmethylene bridge.

The transition metal compound of the present invention is represented by General Formula (1):

(1)

where $M^1$ is a transition metal of Group 4, 5, or 6 of the Periodic Table; $R^1$ is a hydrocarbon or oxygen-containing hydrocarbon group of 1 to 20 carbons, a silicon-containing hydrocarbon group of 3 to 20 carbons, or a nitrogen-containing hydrocarbon group of 2 to 20 carbons; $R^2$, $R^3$, and $R^4$ are respectively independently a hydrogen atom, a hydrocarbon or oxygen-containing hydrocarbon group of 1 to 20 carbons, a silicon-containing hydrocarbon group of 3 to 20 carbons, or a nitrogen-containing hydrocarbon group of 2 to 20 carbons; $R^5$, and $R^6$ are independently an aryl group of 6 to 10 carbons; $R^7$ and $R^8$ are respectively a substituent on the benzo ring of the fluorenyl group, and are independently a hydrocarbon or oxygen-containing hydrocarbon group of 1 to 20 carbons, an amino group of 2 to 20 carbons, or a halogen atom; $Q^1$, and $Q^2$ are independently a hydrogen atom, a halogen atom, a hydrocarbon or oxygen-containing hydrocarbon group of 1 to 20 carbons, or an amino group of 2 to 20 carbons; and m, and n are independently an integer of 0 to 4.

The present invention also relates to a process for producing the transition metal compound, an olefin polymerization catalyst containing the transition metal compound, and a process for producing an olefin polymer.

DETAILED DESCRIPTION OF THE PREFERRED EMBODIMENT

The transition metal compound of the present invention is represented by General Formula (1) below:

(1)

In General Formula (1), $M^1$ is a transition metal of Group 4, 5, or 6 of the Periodic Table, specifically including titanium, zirconium, hafnium, vanadium, niobium, tantalum, chromium, molybdenum, and tungsten; preferably titanium, zirconium, and hafnium.

$R^1$ is a hydrocarbon or oxygen-containing hydrocarbon group of 1 to 20 carbons, a silicon-containing hydrocarbon group of 3 to 20 carbons, or a nitrogen-containing hydrocarbon group of 2 to 20 carbons. The hydrocarbon group of 1 to 20 carbons includes alkyl groups such as methyl, ethyl, propyl, butyl, pentyl, hexyl, heptyl, octyl, nonyl, decyl, dodecyl, isopropyl, isobutyl, s-butyl, t-butyl, and cyclohexyl; alkenyl groups such as vinyl, propenyl, and cyclohexenyl; aryl groups such as phenyl, methylphenyl, ethylphenyl, biphenyl, and naphthyl; and arylalkyl groups such as benzyl, and phenylethyl. The oxygen-containing hydrocarbon group of 1 to 20 carbons includes alkoxyalkyl groups such as methoxymethyl, and 2-methoxyethyl; alkoxy groups such as methoxy, and ethoxy; aryloxy groups such as phenoxy, and methylphenoxy; arylalkoxy groups such as phenylmethoxy, and phenylethoxy; and acyl groups such as acetyl, and benzoyl. The silicon-containing hydrocarbon group of 3 to 20 carbons includes alkylsilyl groups such as trimethylsilyl, and triethylsilyl; and arylsilyl groups such as phenyldimethylsilyl, and diphenylmethylsilyl. The nitrogen-containing hydrocarbon group of 2 to 20 carbons includes amino groups such as dimethylamino, diethylamino, and dipropylamino; aminoalkyl groups such as dimethylaminoethyl, and dimethylaminopropyl; and aminoaryl groups such as dimethylaminophenyl.

$R^2$, $R^3$, and $R^4$ are respectively independently a hydrogen atom, a hydrocarbon or oxygen-containing hydrocarbon group of 1 to 20 carbons, a silicon-containing hydrocarbon group of 3 to 20 carbons, or a nitrogen-containing hydrocarbon group of 2 to 20 carbons. Specific examples of the groups of $R^2$, $R^3$, and $R^4$ other than the hydrogen atom are the same as the hydrocarbon groups, the oxygen-containing hydrocarbon groups, and the nitrogen-containing hydrocarbon mentioned for the above $R^1$ group.

$R^5$ and $R^6$ are respectively a substituent of the methylene bridge between the substituted cyclopentadienyl group and the fluorenyl group, and are independently an aryl group of 6 to 10 carbons, specifically including aryl groups of phenyl, tolyl, xylyl, cumenyl, mesityl, naphthyl, and methoxyphenyl.

$R^7$ and $R^8$ are respectively a substituent on the benzo ring of the fluorenyl group, and are independently a hydrocarbon or oxygen-containing hydrocarbon group of 1 to 20 carbons, an amino group of 2 to 20 carbons, or a halogen atom. Specifically, the hydrocarbon group of 1 to 20 carbons includes alkyl groups such as methyl, ethyl, propyl, pentyl, hexyl, heptyl, decyl, isopropyl, isobutyl, s-butyl, and t-butyl; aryl groups such as phenyl, and tolyl; and arylalkyl groups such as benzyl. The oxygen-containing hydrocarbon group of 1 to 20 carbons includes alkoxy groups such as methoxy, ethoxy, propoxy, butoxy, and isopropoxy; aryloxy groups such as phenoxy, and methylphenoxy; and arylalkoxy groups such as phenylmethoxy, and phenylethoxy. The amino group of 2 to 20 carbons includes dimethylamino, diethylamino, dipropylamino, dibutylamino, diisopropylamino, diisobutylamino, diisoamylamino, diphenylamino, methylphenylamino, ethylphenylamino, ditolylamino, methyltolylamino, dibenzylamino, and benzylmethylamino. The halogen atom includes fluorine, chlorine, bromine, and iodine.

$Q^1$, and $Q^2$ are independently a hydrogen atom, a halogen atom, a hydrocarbon or oxygen-containing hydrocarbon group of 1 to 20 carbons, or an amino group of 2 to 20 carbons. Specific examples of $Q^1$ and $Q^2$ other than the hydrogen atom are the same as the hydrocarbon or oxygen-containing hydrocarbon group of 1 to 20 carbons, the amino group of 2 to 20 carbons, and the halogen atom mentioned for $R^7$ and $R^8$.

The symbols m and n showing the number of the substituents on the benzo rings of the fluorenyl group are independently an integer of 0 to 4.

The transition metal compound is specifically exemplified by the compounds below:

diphenylmethylene(3-methylcyclopentadienyl)(fluorenyl)zirconium dichloride,
diphenylmethylene(3-methylcyclopentadienyl)(fluorenyl)dimethylzirconium,
diphenylmethylene(3-ethylcyclopentadienyl)(fluorenyl)zirconium dichloride,
diphenylmethylene(3-ethylcyclopentadienyl)(fluorenyl)dimethylzirconium,
diphenylmethylene(3-propylcyclopentadienyl)(fluorenyl)zirconium dichloride,
diphenylmethylene(3-propylcyclopentadienyl)(fluorenyl)dimethylzirconium,
diphenylmethylene(3-butylcyclopentadienyl)(fluorenyl)zirconium dichloride,
diphenylmethylene(3-butylcyclopentadienyl)(fluorenyl)dimethylzirconium,
diphenylmethylene(3-isopropylcyclopentadienyl)(fluorenyl)zirconium dichloride,
diphenylmethylene(3-isopropylcyclopentadienyl)(fluorenyl)dimethylzirconium,
diphenylmethylene(3-isobutylcyclopentadienyl)(fluorenyl)zirconium dichloride,
diphenylmethylene(3-isobutylcyclopentadienyl)(fluorenyl)dimethylzirconium,
diphenylmethylene(3-s-butylcyclopentadienyl)(fluorenyl)zirconium dichloride,
diphenylmethylene(3-s-butylcyclopentadienyl)(fluorenyl)dimethylzirconium,
diphenylmethylene(3-t-butylcyclopentadienyl)(fluorenyl)zirconium dichloride,
diphenylmethylene(3-t-butylcyclopentadienyl)(fluorenyl)dimethylzirconium,
diphenylmethylene(3-vinylcyclopentadienyl)(fluorenyl)zirconium dichloride,
diphenylmethylene(3-vinylcyclopentadienyl)(fluorenyl)dimethylzirconium,
diphenylmethylene(3-allylcyclopentadienyl)(fluorenyl)zirconium dichloride,
diphenylmethylene(3-allylcyclopentadienyl)(fluorenyl)dimethylzirconium,
diphenylmethylene(3-phenylcyclopentadienyl)(fluorenyl)zirconium dichloride,
diphenylmethylene(3-phenylcyclopentadienyl)(fluorenyl)dimethylzirconium,
diphenylmethylene(3-mesitylcyclopentadienyl)(fluorenyl)zirconium dichloride,
diphenylmethylene(3-mesitylcyclopentadienyl)(fluorenyl)dimethylzirconium,
diphenylmethylene(3-benzylcyclopentadienyl)(fluorenyl)zirconium dichloride,
diphenylmethylene(3-benzylcyclopentadienyl)(fluorenyl)dimethylzirconium,
diphenylmethylene(3-(dimethylamino)cyclopentadienyl)(fluorenyl)zirconium dichloride,
diphenylmethylene(3-(dimethylamino)cyclopentadienyl)-(fluorenyl)dimethylzirconium,
diphenylmethylene(3-(methoxymethyl)cyclopentadienyl)-(fluorenyl)zirconium dichloride,
diphenylmethylene(3-(methoxymethyl)cyclopentadienyl)-(fluorenyl)dimethylzirconium,.
diphenylmethylene(3,4-dimethylcyclopentadienyl)(fluorenyl)-zirconium dichloride,
diphenylmethylene(3,4-dimethylcyclopentadienyl)(fluorenyl)-dimethylzirconium,
diphenylmethylene(3-methyl-4-ethylcyclopentadienyl)(fluorenyl)zirconium dichloride,
diphenylmethylene(3-methyl-4-ethylcyclopentadienyl)(fluorenyl)dimethylzirconium,
diphenylmethylene(3,4-dibenzylcyclopentadienyl)(fluorenyl)-zirconium dichloride,
diphenylmethylene(3,4-dibenzylcyclopentadienyl)(fluorenyl)-dimethylzirconium,
diphenylmethylene(3,4-diphenylcyclopentadienyl)(fluorenyl)-zirconium dichloride,
diphenylmethylene(3,4-diphenylcyclopentadienyl)(fluorenyl)-dimethylzirconium,
diphenylmethylene(2,3,4-trimethylcyclopentadienyl)-(fluorenyl)zirconium dichloride,
diphenylmethylene(3-methyl-4-benzylcyclopentadienyl)(fluorenyl)zirconium dichloride,
diphenylmethylene(3-methyl-4-benzylcyclopentadienyl)(fluorenyl)dimethylzirconium,
diphenylmethylene(2,3,4-trimethylcyclopentadienyl)-(fluorenyl)dimethylzirconium,
diphenylmethylene(3-methylcyclopentadienyl)(2,7-dimethylfluorenyl)zirconium dichloride,
diphenylmethylene(3-methylcyclopentadienyl)(2,7-dimethylfluorenyl)dimethylzirconium,
diphenylmethylene(3,4-dimethylcyclopentadienyl) (2,7-dimethylfluorenyl)zirconium dichloride,
diphenylmethylene(3,4-dimethylcyclopentadienyl) (2,7-dimethylfluorenyl)dimethylzirconium,
diphenylmethylene(3-methylcyclopentadienyl) (2,7-di-t-butylfluorenyl)zirconium dichloride,
diphenylmethylene(3-methylcyclopentadienyl) (2,7-di-t-butylfluorenyl)dimethylzirconium,
diphenylmethylene(3,4-dimethylcyclopentadienyl) (2,7-di-t-butylfluorenyl)zirconium dichloride,
diphenylmethylene(3,4-dimethylcyclopentadienyl) (2,7-di-t-butylfluorenyl)dimethylzirconium,
diphenylmethylene(3-methylcyclopentadienyl)(2-methoxyfluorenyl)zirconium dichloride, diphenylmethylene(3-methylcyclopentadienyl)(2-methoxyfluorenyl)dimethylzirconium, diphenylmethylene(3,4-dimethylcyclopentadienyl)(2-methoxyfluorenyl)zirconium dichloride, diphenylmethylene(3,4-dimethylcyclopentadienyl)(2-methoxyfluorenyl)dimethylzirconium, diphenylmethylene(3-methylcyclopentadienyl)(4-methoxyfluorenyl)zirconium dichloride, diphenylmethylene(3-methylcyclopentadienyl)(4-methoxyfluorenyl)dimethylzirconium, diphenylmethylene(3,4-dimethylcyclopentadienyl)(4-methoxyfluorenyl)zirconium dichloride, diphenylmethylene(3,4-dimethylcyclopentadienyl)(4-methoxyfluorenyl)dimethylzirconium, diphenylmethylene(3-methylcyclopentadienyl)(2-(dimethylamino)fluorenyl)zirconium dichloride, diphenylmethylene(3-methylcyclopentadienyl)(2-(dimethylamino)fluorenyl)dimethylzirconium, diphenylmethylene(3,4-dimethylcyclopentadienyl)(2-(dimethylamino)fluorenyl)zirconium dichloride, diphenylmethylene(3,4-dimethylcyclopentadienyl)(2-(dimethylamino)fluorenyl)dimethylzirconium, diphenylmethylene(3-methylcyclopentadienyl)(4-(dimethylamino)fluorenyl)zirconium dichloride, diphenylmethylene(3-methylcyclopentadienyl)(4-(dimethylamino)fluorenyl)dimethylzirconium, diphenylmethylene(3,4-dimethylcyclopentadienyl)(4-(dimethylamino)fluorenyl)zirconium dichloride, and diphenylmethylene(3,4-dimethylcyclopentadienyl)(4-(dimethylamino)fluorenyl)dimethylzirconium; and the compounds derived by replacing zirconium as the central metal by titanium, or hafnium, but are not limited thereto.

The transition metal compound of the present invention can be derived through the following reactions:

The compound represented by General Formula (2) in which an unsubstituted cyclopentadiene group and a fluorene derivative group are linked by a diarylmethylene group can be synthesized by a known process such as the one disclosed in JP-A-2-274703. The compound of General Formula (2) may be an isomer thereof having the double bonds at different positions in the cyclopentadienyl ring, or a mixture of the isomers.

For introducing the substituent such as a hydrocarbon group, an oxygen-containing hydrocarbon group, and a nitrogen-containing hydrocarbon group to the cyclopentadienyl ring, the compound of General Formula (2) is firstly deprotonized by a basic compound represented by General Formula (3) in an inert solvent to obtain a metal salt of a monoanion of Compound (2).

In General Formula (3), $R^9$ is a hydrogen atom, or a hydrocarbon group of 1 to 10 carbons such as methyl, ethyl, propyl, and butyl; $M^2$ is an alkali metal such as Li, Na, and K, or an alkaline earth metal such as Mg; $Q^3$ is a halogen atom; y is the valency of $M^2$, and is 1 or 2; and x is an integer of 1 or 2. Specific examples of the compound of General Formula (3) include metal hydrides such as lithium hydride, sodium hydride, and potassium hydride; and organometallic compounds such as methyllithium, butyllithium, phenyllithium, methylmagnesium bromide, methylmagnesium iodide, ethylmagnesium bromide, and isopropylmagnesium bromide; but are not limited thereto. Any basic compound other than Compound (3) which can abstract a proton from the cyclopentadienyl ring of Compound (2) may be used in place of Compound (3).

The metal salt of the monoanion formed by the reaction of Compound (2) and Compound (3) need not be isolated, and is allowed to react with a reagent represented by General Formula (4) to obtain the compound represented by General Formula (5') in which a cyclopentadienyl group having one substituent, and a fluorene group are linked by a diarylmethylene group. To Compound (5') having a monosubstituted cyclopentadienyl ring, a further substituent or substituents which may be the same as or different from the aforementioned substituent can be introduced by using Compound (3) and Compound (4) (Compound (4) may be different from the one used above) successively to obtain Compound (5) having the same or different plural substituents.

In General Formula (4), $R^1$ is a hydrocarbon or oxygen-containing hydrocarbon group of 1 to 20 carbons, a silicon-containing hydrocarbon group of 3 to 20 carbons, or a nitrogen-containing hydrocarbon group of 2 to 20 carbons. $Q^4$ is a group releasable by reaction with a nucleophilic reagent, exemplified by halogen atoms such as fluorine, chlorine, bromine, and iodine; and sulfonic anions such as tosyl and mesyl.

In General Formula (5), $R^1$ is a hydrocarbon or oxygen-containing hydrocarbon group of 1 to 20 carbons, a silicon-containing hydrocarbon group of 3 to 20 carbons, or a nitrogen-containing hydrocarbon group of 2 to 20 carbons; $R^2$, $R^3$, and $R^4$ are independently a hydrogen atom, a hydrocarbon or oxygen-containing hydrocarbon group of 1 to 20 carbons, a silicon-containing hydrocarbon group of 3 to 20 carbons, or a nitrogen-containing hydrocarbon group of 2 to 20 carbons; $R^5$, and $R^6$ are independently an aryl group of 6 to 10 carbons; $R^7$, and $R^8$ are respectively a substituent on the benzo ring of the fluorenyl group, and are independently a hydrocarbon or oxygen-containing hydrocarbon group of 1 to 20 carbons, an amino group of 2 to 20 carbons, or a halogen atom; and m, and n are independently an integer of 0 to 4. The compound of General Formula (5) may be an isomer thereof having the double bonds at other positions in the cyclopentadienyl ring, or a mixture of the isomers.

The ligand having the substituents on the cyclopentadienyl ring is synthesized under the conditions shown below. Compound (3) for deprotonation is used in a sufficient amount for forming the metal salt of the monoanion of Compound (2): in an amount of not less than one equivalent, preferably one equivalent to Compound (2). Compound (4) to be reacted with the resulting anion is used in an amount of not less than one equivalent to the anion. When Compound (4) is not readily isolatable from Compound (5), the amount is preferably one equivalent. If Compound (3) is used in an amount excessive to Compound (2), a dianion can be formed, and the substituent can be introduced also to the 9-position of the fluorenyl group, which may prevent the function of the fluorenyl group as the ligand of the transition metal compound. Otherwise, if Compound (3) is not sufficient, Compound (2) remains nonanionized to form a mixture of the compounds substituted and unsubstituted at the cyclopentadienyl ring moiety, which necessitates separation of the mixture. When one equivalent of a base represented by Compound (3) is reacted with Compound (2), the proton of the cyclopentadienyl moiety is expected to be eliminated to form a monoanion, since the proton of a cyclopentadienyl group is generally more strongly acidic than the proton of a fluorenyl group. If Compound (4) is used in an amount of less than one equivalent to the monoanion of Compound (2), a mixture of the compounds substituted and unsubstituted at the cyclopentadienyl ring moiety is formed, which necessitates separation of the mixture.

The reaction of formation of the metal salt of the monoanion is preferably conducted in an inert solvent. The solvent includes aliphatic hydrocarbons such as hexane, aromatic hydrocarbons such as toluene, and ethers such as diethyl ether, and tetrahydrofuran.

The temperature of the reaction is in the range of from −100 to 40° C. where the metal salt of the anion is stable.

The transition metal compound (1) is formed from Compound (5) by a known process. The ligand compound (5) is reacted with two equivalents of a base capable of deprotonation like Compound (3) to form a metal salt of the dianion. This dianion is reacted with a transition metal halide like zirconium tetrachloride to form a transition metal compound of General Formula (1). If necessary, X other than the halogen can be introduced to the transition metal compound of General Fromula (1) by reaction with a reagent like methyllithium.

The present invention also provides an olefin polymerization catalyst prepared from the transition metal compound having a substituted cyclopentadienyl group, a compound to be reacted with the transition metal compound to form a cationic transition metal compound, and optionally an organometallic compound. The compound to be reacted with the transition metal compound to form the cationic transition metal compound, and the optionally employed organometallic compound are described below.

The compound to be reacted to convert the transition metal compound to the cationic transition metal compound includes protonic acids (6), Lewis acids (7), ionizing ionic compounds (8), Lewis acidic compounds (9), and aluminoxanes (10) and (11), and clay minerals (12).

In use of the transition metal for the catalyst, an organometallic compound (13) having one or more alkyl groups may be used as a solvent-like medium for the formation reaction of the cationic transition metal compound including alkylation and hydrogenation, and protection from or reaction with a catalyst poison of the formed cationic transition compound.

The protonic acid use in the present invention is represented by General Formula (6) below:

(6)

where H is a proton, each $L^1$ is a Lewis base independently, $0 < l \leq 2$, $M^3$ is a boron, aluminum, or gallium atom, and each $R^{10}$ is independently a halogen-substituted aryl group of 6 to 20 carbons.

The Lewis acid is represented by General Formula (7) below:

(7)

where $Z^{10}$ is a carbonium cation or a tropylium cation, $M^3$ is a boron, aluminum, or gallium atom, and each $R^{10}$ is independently a halogen-substituted aryl group of 6 to 20 carbons.

The ionizing ionic compound is represented by General Formula (8) below:

$$[M^4L^2_r][M^3R^{10}_4] \quad (8)$$

where $M^4$ is a cation of a metal selected from Groups 1, 2, 8, 9, 10, 11, and 12 of the Periodic Table; $L^2$ is a Lewis base or a cyclopentadienyl group; $0 \leq r \leq 2$; $M^3$ is a boron, aluminum, or gallium atom; and each $R^{10}$ is independently a halogen-substituted aryl group of 6 to 20 carbons.

The Lewis acidic compound is represented by General Formula (9) below:

$$[M^3R^{10}_3] \quad (9)$$

where $M^3$ is a boron, aluminum, or gallium atom, and each $R^{10}$ is independently a halogen-substituted aryl group of 6 to 20 carbons.

Specific examples of the protonic acid represented by General Formula (6) include diethyloxonium tetrakis(pentafluorophenyl)borate, dimethyloxonium tetrakis(pentafluorophenyl)borate, tetramethyleneoxonium tetrakis(pentafluorophenyl) borate, N,N-dimethylanilinium tetrakis(pentafluorophenyl) borate, tri-n-butylammonium tetrakis(pentafluorophenyl)borate, diethyloxonium tetrakis(pentafluorophenyl)aluminate, dimethyloxonium tetrakis(pentafluorophenyl)aluminate, tetramethyleneoxonium tetrakis(pentafluorophenyl) aluminate, N,N-dimethylanilinium tetrakis(pentafluorophenyl) aluminate, and tri-n-butylammonium tetrakis(pentafluorophenyl) aluminate, but are not limited thereto.

Specific examples of the Lewis acid represented by General Formula (7) include trityl tetrakis(pentafluorophenyl)borate, trityl tetrakis(pentafluorophenyl)aluminate, tropylium tetrakis(pentafluorophenyl)borate, and tropylium tetrakis(pentafluorophenyl)aluminate, but are not limited thereto.

Specific examples of the ionizing ionic compound represented by General Formula (8) include lithium salts and ether complexes thereof such as lithium tetrakis(pentafluorophenyl)borate, and lithium tetrakis(pentafluorophenyl)aluminate;

ferrocenium salts such as ferrocenium tetrakis(pentafluorophenyl)borate, and ferrocenium tetrakis(pentafluorophenyl)aluminate; and silver salts such as silver tetrakis(pentafluorophenyl)borate, and silver tetrakis(pentafluorophenyl)aluminate, but are not limited thereto.

Specific examples of the Lewis acidic compound represented by General Formula (9) include tris(pentafluorophenyl)borane, tris (2,3,5,6-tetraphenyl)borane, tris (2,3,4,5-tetraphenyl)borane, tris(3,4,5-triphenyl)borane, phenyl-bis(pentafluorophenyl)borane, and tris(3,4,5-triphenyl)aluminum, but are not limited thereto.

The aluminoxane used in the present invention may be in a linear form represented by General Formula (10) or in a cyclic form represented by General Formula (11):

where p is an integer of 2 or more; the groups $R^{11}$ are independently a hydrocarbon group, an alkylamino group, or a methoxy group, and at least one $R^{11}$ is a hydrocarbon group of 1 to 20 such as methyl, ethyl, propyl, butyl, octyl, isopropyl, isobutyl, decyl, dodecyl, tetradecyl, and hexadecyl.

The clay mineral used in the present invention is an inorganic polymer compound constituted of tetrahedrons formed by coordination of oxygen ions to silicon ions and an octahedron formed by coordination of oxygen or hydroxyl ions to ions such as aluminum ions, magnesium ions, and iron ions. Most of the clay minerals have a skeleton structure which is not neutral electrically and has a positive or negative charge on the surface, and has a cation to compensate for the negative charge. This cation is exchangeable for another cation. The clay mineral used in the present invention has such a cation exchange ability, specifically including kaolin minerals such as kaolinite, dickite, halloysite; smectites such as montmorillonite, hectorite, beidelite, saponite, teniolite, and sauconite; micas such as muscovite, palagonite, and illite; vermiculite; brittle micas such as margarite, and klintonite; chlorites such as donbassite, cookeite, and clinochlore; sepiolites; and palygorskites, but is not limited thereto. These clay minerals exist as natural resources, and can also be synthesized artificially with higher purity. The above-mentioned natural clays and artificial clays are useful in the present invention.

The clay mineral used in the present invention is preferably treated chemically preliminarily. The chemical treatment includes acid or alkali treatment, salt treatment, and complex formation by treatment with an organic or inorganic compound. The acid or alkali treatment not only removes impurities but also extracts a part of the metal cation in the crystal structure of the clay mineral or destroys the crystal structure to make the clay mineral amorphous. The acid used for the acid treatment includes Bronsted acids such as hydrochloric acid, sulfuric acid, nitric acid, and acetic acid. The alkali used therefor includes sodium hydroxide, potassium hydroxide, and calcium hydroxide.

By the complex formation by the salt treatment or the reaction with the organic or inorganic compound, a new clay compound having different properties can be formed by cation exchange without destruction of the basic crystal structure. The compound used for the salt treatment includes ionic halogen compounds such as sodium chloride, potassium chloride, lithium chloride, magnesium chloride, aluminum chloride, iron chloride, and ammnoim chloride; sulfate salts such as sodium sulfate, potassium sulfate, aluminum sulfate, and ammonium sulfate; carbonates such as calcium carbonate, sodium carbonate, and potassium carbonate; phosphates such as sodium phosphate, potassium phosphate, aluminum phosphate, and ammonium phosphate; and the like inorganic salts, and organic salts such as sodium acetate, potassium acetate, potassium oxalate, sodium citrate, and sodium tartarate.

The organic compound used for synthesis of the organic complex of the clay mineral includes the onium salts mentioned later, compounds capable of forming a carbonium cation such as trityl chloride and tropylium bromide; and complex compounds capable of forming a metal complex cation such as ferrocenium salts. The inorganic compound used for synthesis of the inorganic complex of the clay mineral includes metal hydroxides capable of forming a hydroxide cation such as aluminum hydroxide, zirconium hydroxide, and chromium hydroxide.

Particularly preferred clay minerals used in the present invention include modified clay minerals which are clay minerals/organic ion complexes formed by exchanging an exchangeable cation in the clay mineral for a specific organic cation component. The organic cation to be introduced to form the modified clay compound includes specifically aliphatic ammonium cations such as butylammonium, hexylammonium, decylammonium, dodecylammonium, diamylammonium, tributylammonium, and N,N-dimethyldecylammoniumi aromatic ammonium cations such as anilinium, N-methylanilium, N,N-dimethylanilium, N-ethylanilinium, benzylammonium, toluidinium, dibenzylammonium, tribenzylammonium, N,N,2,4,6-pentamethylanilinium; and like ammonium ions; and oxonium ions such as dimethyloxonium, diethyloxonium, but are not limited thereto. The clay mineral is allowed to react with an onium compound constituted of the organic cation to introduce the organic cation by exchange with the exchangeable cation into the clay mineral. The onium compound includes specifically aliphatic amine hydrochlorides such as propylamine hydrochloride, isopropylamine hydrochloride, butylamine hydrochloride, hexylamine hydrochloride, decylamine hydrochloride, docecylamine hydrochloride, diamylamine hydrochloride, tributylamine hydrochloride, triamylamine hydrochloride, N,N-dimethyldecylamine hydrochloride, and N,N-dimethylundecylamine hydrochloride; aromatic amines such as aniline hydrochloride, N-methylaniline hydrochloride, N,N-dimethylaniline hydrochloride, N-ethylaniline hydrochloride, N,N-diethylaniline hydrochloride, o-toluidine hydrochloride, p-toluidine hydrochloride, N-methyl-o-toluidine hydrochloride, N-methyl-p-toluidine hydrochloride, N,N-dimethyl-o-toluidine hydrochloride, N,N-dimethyl-p-toluidine hydrochloride, benzylamine hydrochloride, dibenzylamine hydrochloride, and N,N,2,4,6-pentamethylaniline hydrochloride; hydrofluorides, hydrobromides, hydroiodides, and sulfates of the above amines instead of the hydrochlorides; and oxonium compounds such as methyl ether hydrochloride, ethyl ether hydrochloride, and phenyl ether hydrochloride, but is not limited thereto. Of the onium compounds including the ammonium compounds and the oxonium compounds, ammonium compounds are used preferably, and aromatic amines more preferably.

The onium compound to be reacted with the clay mineral may be isolated preliminarily, or can be formed in situ in the reaction solvent for the reaction with the clay mineral by contact of a heteroatom-containing compound such as amines, ethers, and sulfides with a protonic acid such as hydrofluoric acid, hydrochloric acid, hydrobromic acid, hydroiodic acid, and sulfuric acid, and used without separation. The conditions for the reaction of the clay mineral with the onium compound for the modification of the clay mineral is not especially limited. The ratio of the amount of the onium compound to be reacted is not especially limited, but is preferably not less than 0.5 equivalent, more preferably not less than 1 equivalent, to the cation existing in the clay mineral. The clay mineral may be used singly, or in a mixture of two or more thereof. The reaction solvent for the modification is exemplified by water, and polar organic solvents including specifically alcohols such as methyl alcohol, and ethyl alcohol; acetone, tetrahydrofuran, N,N-dimethylformamide, dimethylsulfoxide, and methylene chloride. The solvent may be used singly or in a mixture thereof. Of the above solvents, water and alcohols are preferred.

The protonic acid (6), the Lewis acid (7), the ionizing ionic compound (8), the Lewis acidic compound (9), the aluminoxane (10), (11), and the clay mineral (12) employed as the constituents of the catalyst of the present invention are capable of reacting with the above transition metal compound to form a cationic transition metal compound, and to give a counter anion to the formed cationic transition metal compound.

The organometallic compound employed in the present invention includes organometals composed of an element of Group 1, 2, or 13 of the Periodic Table, tin or zinc: specifically including the one represented by General Formula (13) below:

$$[M^5R^{12}{}_s] \tag{13}$$

wherein $M^5$ is an element of Group 1, Group 2, or Group 13 of the Periodic Table, Sn, or Zn; each of $R^{12}$ is independently a hydrogen atom, an alkyl, or alkoxy group of 1 to 24 carbons, or an aryl, aryloxy, arylalkyl, arylalkoxy, alkylaryl, or alkylaryloxy group of 6 to 24 carbons, at least one $R^{12}$ being a hydrogen atom, an alkyl group of 1 to 24 carbons, or an aryl, arylalkyl, or alkylaryl group of 6 to 24 carbons; and s is the oxidation number of $M^5$.

The compound represented by General Formula (13) includes organoaluminum compounds such as trimethylaluminum, triethylaluminum, tripsopropylaluminum, tri-n-propylaluminum, triisobutylaluminum, tri-n-butylaluminum, triamylaluminum, dimethylaluminum ethoxide, diethylaluminum ethoxide, diisopropylaluminum ethoxide, di-n-propylaluminum ethoxide, diisobutylaluminum ethoxide, di-n-butylaluminum ethoxide, dimethylaluminum hydride, diethylaluminum hydride, diisopropylaluminum hydride, di-n-propylaluminum hydride, diisobutylaluminum hydride, and di-n-butylaluminum hydride; organolithium compounds such as methyllithium, and butyllithium; organomagnesium compounds such as methylmagnesium bromide, and ethylmagnesium bromide, but is not limited thereto. Of the organometallic compounds organoaluminum compounds are preferred.

The process for preparing the catalyst from the aforementioned catalyst components is not especially limited. For example, the components are mixed in an inert solvent, or in a monomer to be polymerized. The order of contact of the components, and the temperature and time for the treatment are not especially limited, provided that the cationic transition metal compound can be formed.

In the catalyst system, the protonic acid, the Lewis acid, the ionizing ionic compound, and/or the Lewis acidic compound is used in an amounts of preferably from 0.1 to 100 mol, more preferably from 0.5 to 30 mol per mol of the transition metal compound.

The amount of the additionally employed organometallic compound is not especially limited, but is preferably not more than 100000 mol per mol of the transition metal compound. When the amount is larger than that, ash removal is necessary. In consideration of the stability of the cationic transition metal compound, and elimination of the catalyst poison, the additional organometallic compound is used preferably in an amount of from 1 to 10000 mol per mol of the cationic transition metal compound.

The amount of the aluminoxane used in preparation of the catalyst is not especially limited, but is preferably in the range of from 10 to 100000 mol per mol of the transition metal compound. With an amount of the aluminoxane less than the above range, the cationic transition metal compound is less stable, whereas with an amount larger than the above range, ash removal from the produced polymer is necessary. More preferably the amount of the aluminoxane is in the range of from 10 to 10000 mol per mol of the transition metal compound. Further, an organoaluminum compound represented by General Formula (13) may be mixed with the aluminoxane or the transition metal compound. The amount of the organoaluminum compound used is preferably in an amount of not more than 10000 mol per mol of the transition metal to avoid the necessity of ash removal.

The ratio of the clay mineral to the transition metal compound in the catalyst system is not especially limited, provided that the clay mineral is sufficient to react with the transition metal. However, the ratio of the amount of the cation in the clay mineral is preferably in the range of from 1 to 10000 to the transition metal. At the ratio of less than 1, sufficient catalytic activity cannot be achieved, whereas at the ratio of more than 10000, the activity of the catalyst is lower and ash removal from the produced polymer is necessary.

The amount of the organometallic compound as a third component is not especially limited, but the mole ratio thereof to the transition metal compound is preferably not more than 100000. At a larger amount, ash removal is necessary. More preferably the ratio is preferably in the range of from 1 to 10000 for stability of the catalyst and removal of the catalyst poison.

The polymerization by use of the olefin polymerization catalyst of the present invention can be conducted by a usual polymerization process including slurry polymerization, gas-phase polymerization, high-pressure polymerization, solution polymerization, and bulk polymerization.

Two or more of the transition metal compounds of the present invention may be used in combination as the catalyst components for the polymerization.

The solvent, when used, may be any organic solvent usually used for the polymerization. Specifically, the solvent includes benzene, toluene, xylene, butane, pentane, hexane, heptane, cyclohexane, and methylene chloride. The olefin itself such as propylene, 1-butene, 1-octene, and hexene-1 to be polymerized may be used as the solvent.

The olefin which can be polymerized in the present invention includes α-olefins such as ethylene, propylene, 1-butene, 1-pentene, 4-methyl-1-pentene, hexene-1, octene-1, nonene-1, decene-1, and styrene; conjugated and nonconjugated dienes such as butadiene, 1,4-hexadiene, 5-ethylidene-2-norbornene, dicyclopentadiene, 4-methyl-1,4-hexadiene, and 7-methyl-1,6-octadiene; and cyclic olefins such as cyclobutene, but is not limited thereto. The polymerization includes homopolymerization of one olefin and copolymerization of two or more olefins.

In polyolefin production according to the present invention, the polymerization conditions of the temperature, time, pressure, monomer concentration, and so forth are not especially limited. Preferably, the polymerization temperature is in the range of from −100 to 300° C., the polymerization time is in the range of form 10 seconds to 20 hours, and the polymerization pressure is in the range of from ordinary pressure to 3500 kg/cm$^2$G. The molecular weight of the polymer can be controlled by use of hydrogen or the like in the polymerization. The polymerization may be conducted by a batch process, a semicontinuous process, or a continuous process, and may be conducted in two steps of different polymerization conditions. The polyolefin produced by the polymerization is separated from the polymerization solvent and dried by a known method.

In particular, in production of LLDPE composed of ethylene and/or an olefin of 3 or more carbons, or an olefin type elastomer, a high molecular weight of the olefin polymer or copolymer can be obtained by use of the olefin polymerization catalyst of the present invention by a known solution polymerization process or high-temperature and high-pressure polymerization process.

The solution polymerization is conducted under the polymerization conditions below. The polymerization temperature is not especially limited provided that the produced polymer is dissolved at the temperature. The polymer productivity is considered to be improved at a higher polymerization temperature because of lower solution viscosity and ease of removal of the polymerization heat. However, the polymerization temperature is preferably not higher than 300° C. The polymerization temperature is preferably lower to retard a chain transfer reaction which lowers the molecular weight of the polymer, and is more preferably not higher than 250° C. The polymerization pressure is not especially limited, but is preferably in the range of from atmospheric pressure to 200 kg/cm$^2$. The solvent for the polymerization is a usually used organic solvent or the monomer itself as mentioned above.

The high-temperature high-pressure polymerization is conducted under the polymerization conditions below. The polymerization temperature is not limited especially but is not lower than 120° C. The temperature is preferably in the range of from 120 to 300° C. in consideration of the polymer productivity and by the reasons mentioned above for the solution polymerization. The polymerization temperature is more preferably in the range of from 120 to 250° C. to retard the chain transfer reaction which lowers the molecular weight of the polymer. The polymerization pressure is not especially limited, but is preferably in the range of from 500 to 3500 kg/cm$^2$ in view of the polymer productivity.

In the high-pressure process, the reactor may be of a vessel type, a tubular type, or the like.

According to the present invention, an olefin polymer of a high molecular weight can be produced efficiently at such a high temperature that the produced olefin polymer of high molecular weight is melted.

In polymerization of an α-olefin like propylene, various stereospecific polymers such as atactic polypropylene, isotactic polypropylene, hemiisotactic polypropylene, and syndiotactic polypropylene of a high molecular weight can be produced by changing the kind, the substitution position, and the number of the substituents on the cyclopentadienyl ring of the transition metal compound of the catalyst system of the present invention.

The present invention is described in more detail by reference to examples regarding synthesis of the transition metal compound and the results of the polymerization without limiting the invention thereto.

The reaction, the polymerization, and the solvent purification were conducted in an inert gas atmosphere of purified argon or dried nitrogen. The solvents for the reaction were purified, dried, and/or deoxygenated according to known methods. The compounds used for the reactions were synthesized and identified by known methods or modification thereof.

Weight average molecular weight (Mw) and molecular distribution (Qw) of the olefin polymers obtained by the present invention was obtained by gel permeation chromatography (GPC) using a Model 150° C. (manufactured by Waters Co.) with a column of TSK-GEL GMHHR-H (S), and o-dichlorobenzene as the eluent at a measurement temperature of 140° C. and a measurement concentration of 7 mg of the sample in 10 mL of o-dichlorobenzene.

The melt flow rate (MFR) was measured according to ASTM D1238, Condition E.

The transition metal compound and the α-olefin component units were measured by 400 MHz $^1$H-NMR spectrometry, and $^{13}$C-NMR spectrometry with JNMGX400 (manufactured by JEOL Ltd.).

The melting point (Tm) of the olefin polymer was derived by measurement of the crystal melting peak of a sample annealed at 200° C. for 5 minutes and cooled to 0° C. and by elevating the temperature of the sample at 10° C./min with a differential scanning calorimeter (DSC200 manufactured by SEIKO Co.).

EXAMPLE 1
[Synthesis of Diphenylmethylene(3-methylcyclopentadienyl)-(fluorenyl)zirconium Dichloride]

Figure 1:
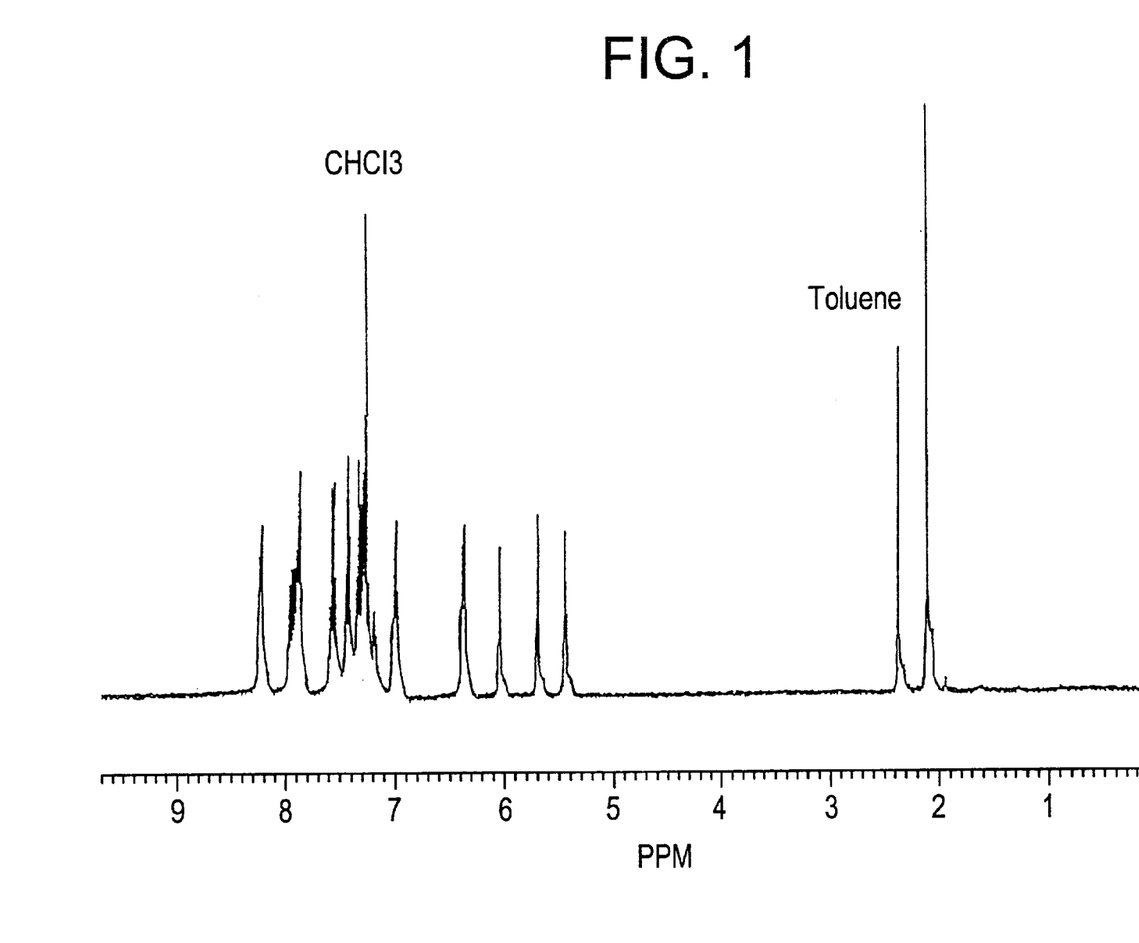
FIG. 1 is a $^1$H-NMR spectrum of diphenylmethylene-(3-methylcyclopentadienyl)(fluorenyl)zirconium dichloride synthesized in Example 1.

In a 100-mL Schlenk vessel, 2.14 g of diphenylmethylene(cyclopentadienyl)-9-fluorene was dissolved in 50 mL of tetrahydrofuran (THF), and the solution was cooled to −78° C. Thereto, 3.2 mL of 1.70M n-butyllithium solution in hexane was added dropwise, and the mixture was stirred for 2 hours. To this solution, 2 mL of methyl iodide was added at −78° C., and the temperature of the solution was allowed to rise overnight spontaneously to room temperature. The solution was extracted by ethyl acetate. The solvent was removed to obtain 2.20 g of a pale yellow solid. 2.04 Grams of this solid was transferred into another Schlenk container, 70 mL of toluene, and 6 mL of THF were added thereto, and the mixture was cooled to 0° C. Then, 6.1 mL of a 1.70M n-butyllithium solution in hexane was added dropwise, and the mixture was left to allow a spontaneous temperature rise to room temperature. To this reaction solution, a liquid suspension of 1.16 g of zirconium tetrachloride in 50 mL toluene was added. After stirring overnight, the hot mixture was filtered. The filtrate was concentrated to obtain a reddish orange solid matter. FIG. 1 shows a $^1$H-NMR chart of this compound.

EXAMPLE 2
[Synthesis of Diphenylmethylene(3-isopropyl-cyclopentadienyl)(fluorenyl)zirconium Dichloride]

Figure 2:
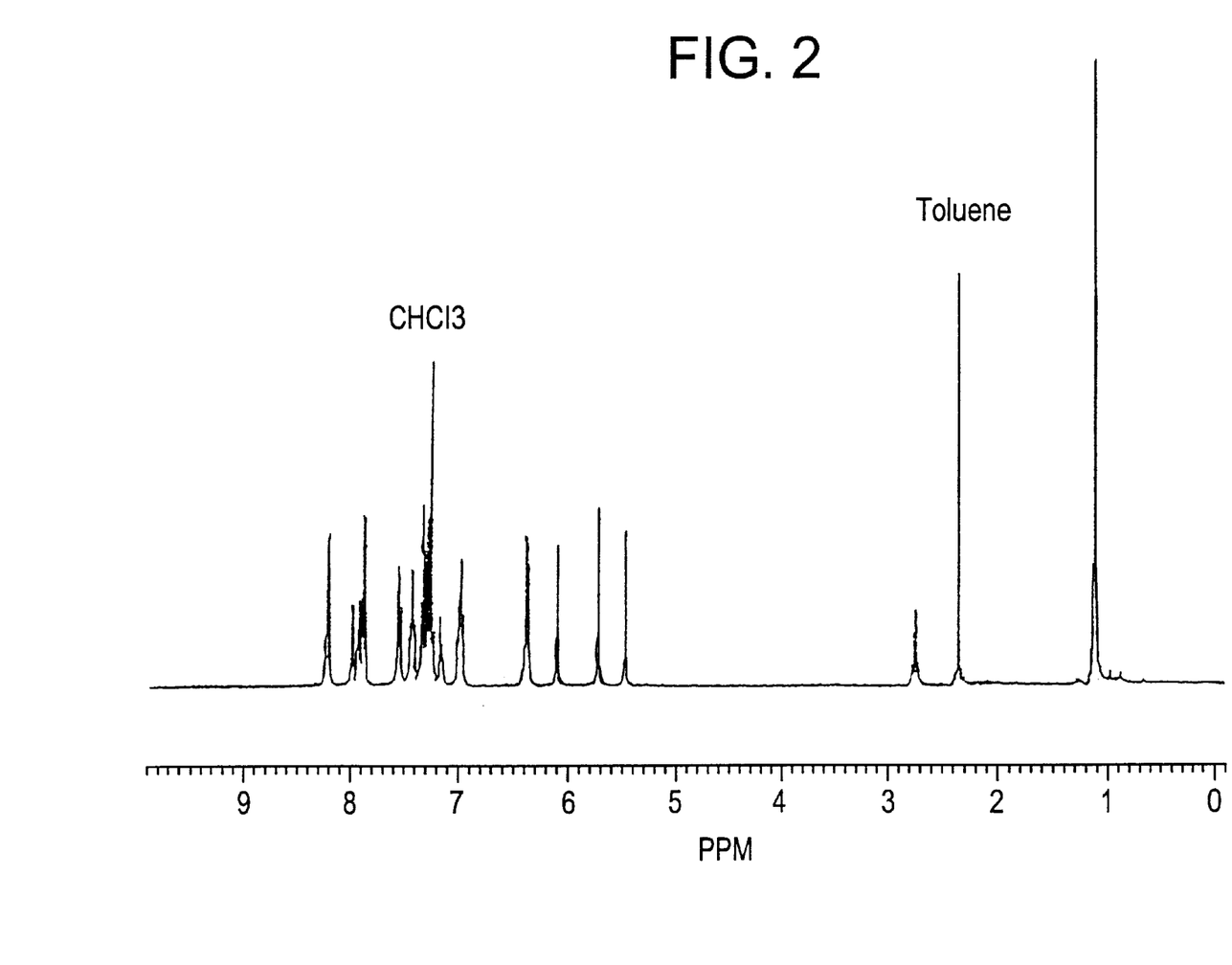
FIG. 2 is a $^1$H-NMR spectrum of diphenylmethylene-(3-isopropylcyclopentadienyl)(fluorenyl)zirconium dichloride synthesized in Example 2.

Synthesis was conducted in the same manner as in EXAMPLE 1 except that isopropyl iodide was used in place of methyl iodide. FIG. 2 shows a $^1$H-NMR chart of the resulting transition metal compound.

EXAMPLE 3
[Synthesis of Diphenylmethylene(3-benzyl-cyclopentadienyl)(fluorenyl)zirconium Dichloride]

Figure 3:
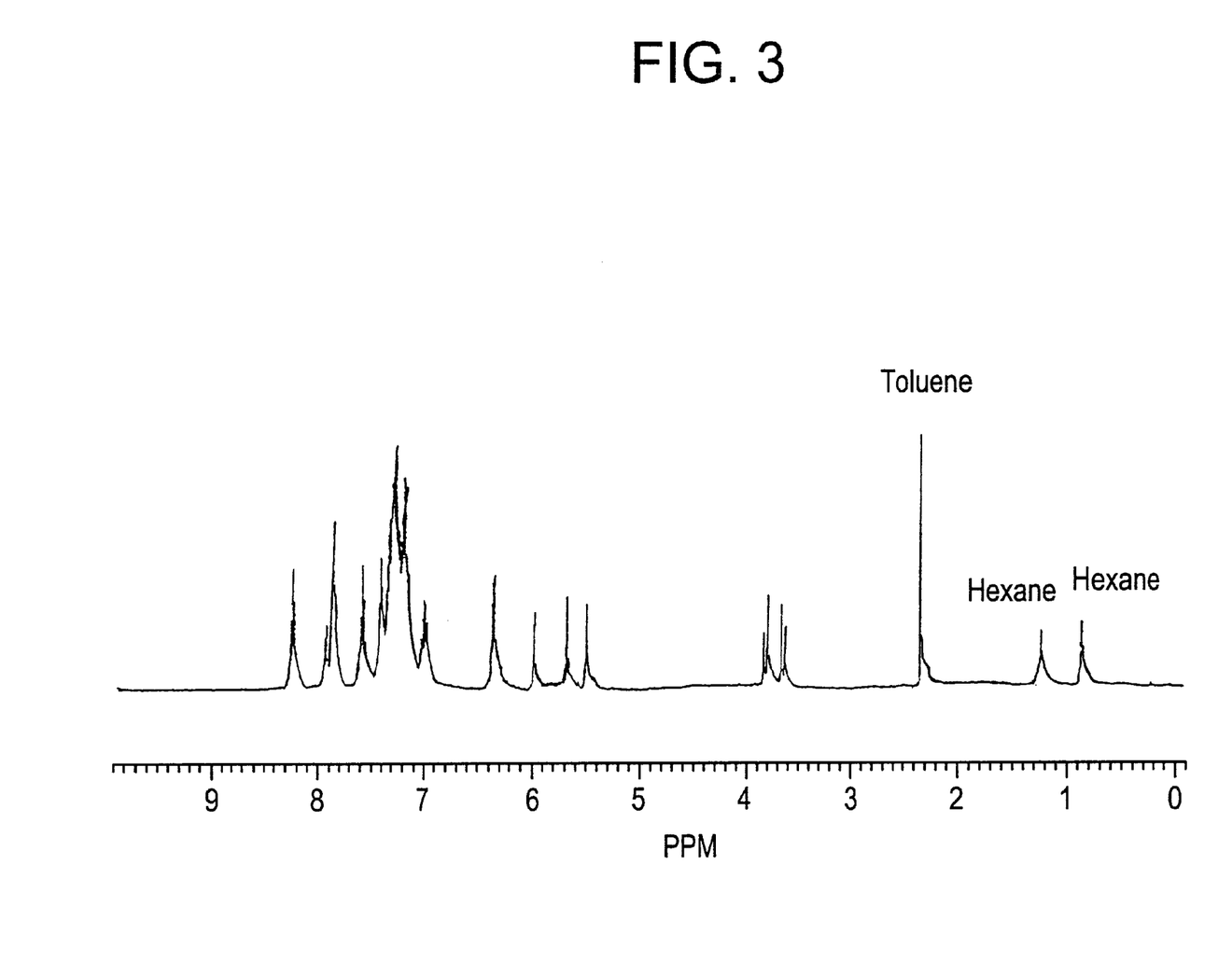
FIG. 3 is a $^1$H-NMR spectrum of diphenylmethylene-(3-benzylcyclopentadienyl)(fluorenyl)zirconium dichloride synthesized in Example 3.

Synthesis was conducted in the same manner as in Example 1 except that benzyl bromide was used in place of methyl iodide. FIG. 3 shows a $^1$H-NMR chart of the resulting transition metal compound.

EXAMPLE 4
[Synthesis of Diphenylmethylene(3-(trimethylsilyl)-cyclopentadienyl)(fluorenyl)zirconium Dichloride]

Figure 4:
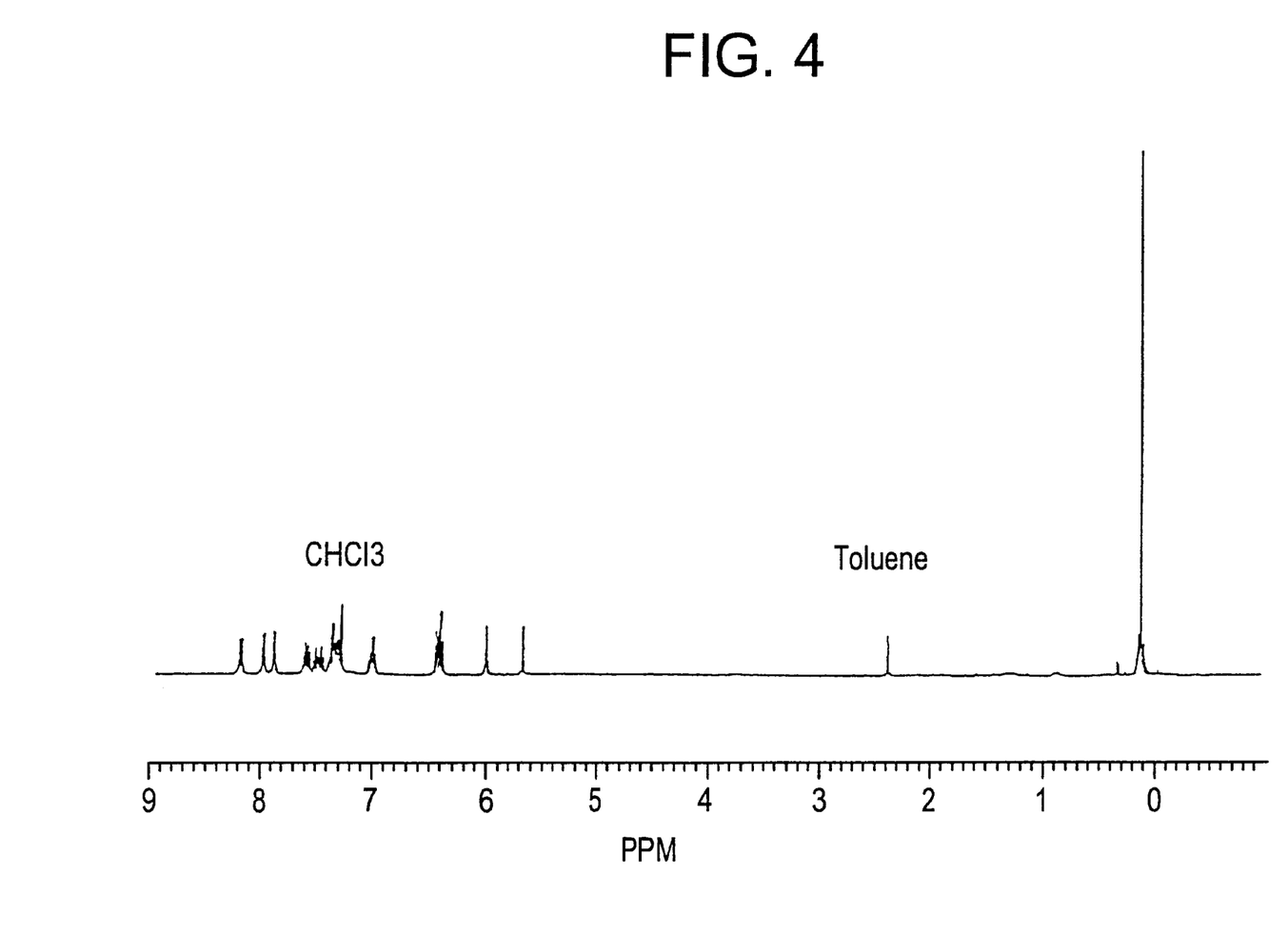
FIG. 4 is a $^1$H-NMR spectrum of diphenylmethylene-(3-(trimethylsilyl)cyclopentadienyl)(fluorenyl)-zirconium dichloride synthesized in Example 4.
Figure 5:
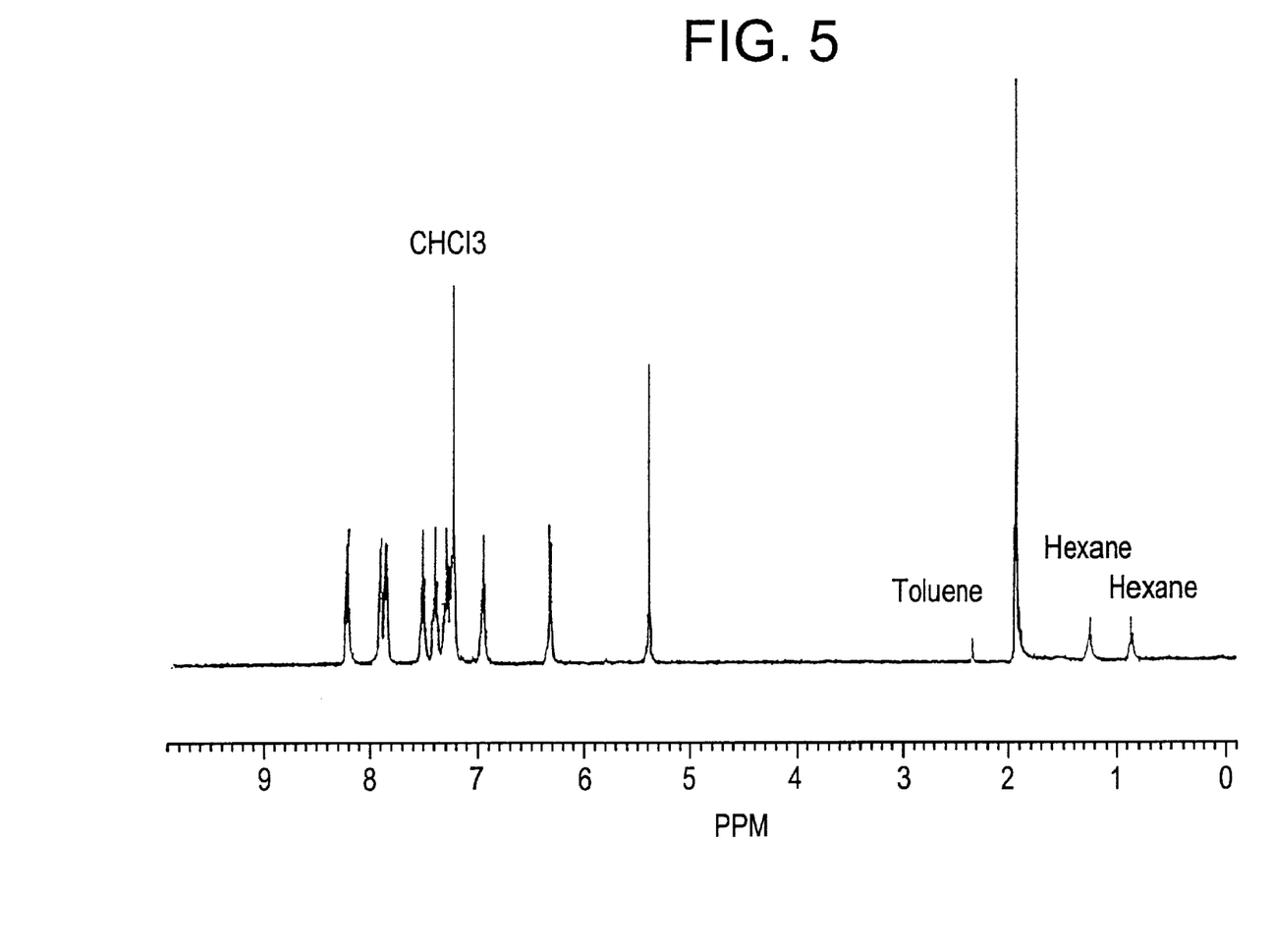
FIG. 5 is a $^1$H-NMR spectrum of diphenylmethylene-(3,4-dimethylcyclopentadienyl)(fluorenyl)zirconium dichloride synthesized in Example 5.

Synthesis was conducted in the same manner as in Example 1 except that trimethylsilyl chloride was used in place of methyl iodide. FIG. 4 shows a $^1$H-NMR chart of the resulting transition metal compound.

EXAMPLE 5
[Synthesis of Diphenylmethylene(3,4-dimethyl-cyclopentadienyl)(fluorenyl)zirconium Dichloride]

In a 100-mL Schlenk vessel 6.58 g of diphenyl-methylene (cyclopentadienyl)-9-fluorene was dissolved in 150 mL of tetrahydrofuran (THF), and the solution was cooled to −78° C. Thereto, 9.8 mL of a 1.70M n-butyllithium solution in hexane was added dropwise, and the mixture was stirred for 2 hours. To this solution, 5 mL of methyl iodide was added at −78° C., and the temperature of the solution was allowed to spontaneously rise overnight with stirring to room temperature. The solution was extracted by ethyl acetate. The solvent was removed to obtain 6.34 g of a pale yellow solid matter. 5.06 Grams of this solid matter was transferred into another Schlenk vessel, and was dissolved by addition of 120 mL of THF. The solution was cooled to −78° C. Then 7.4 mL of a 1.70M n-butyllithium solution in hexane was added dropwise, and the mixture was stirred for 2 hours. To this solution, 5 mL of methyl iodide was added at −78° C., and the temperature was allowed to rise overnight with stirring to room temperature. The reaction mixture was extracted by ethyl acetate, and the solvent was removed to obtain 4.51 g of a pale yellow solid matter. 2.81 Grams of this solid matter was transferred into still another Schlenk vessel. Thereto, 70 mL of toluene and 6 mL of THF were added, and the mixture was cooled to 0° C. Thereto, 8.0 mL of a 1.70M n-butyllithium solution in hexane was added dropwise. The temperature was allowed to rise spontaneously to room temperature. To this reaction solution, a liquid suspension of 1.58 g of zirconium tetrachloride in 50 mL of toluene was added. After stirring overnight, the hot mixture was filtered. The filtrate was concentrated to obtain a solid matter. FIG. 1 shows a $^1$H-NMR chart of this compound.

COMPARATIVE EXAMPLE 1

In a 300-mL Schlenk vessel 5.14 g of fluorene was dissolved in 100 mL of THF, and the solution was cooled to −78° C. Thereto, 20 mL of a 1.64M n-butyllithium solution in hexane was added dropwise with stirring, and the temperature of the reaction mixture was allowed to rise overnight. It was cooled to −78° C, and 7.53 g of 3-methyl-6,6-diphenylfluvene in 100 mL of THF was added thereto. The temperature was allowed to rise overnight to room temperature. The mixture was stirred further for 2 days. The mixture was further heated, and allowed to react under reflux. However, the fluorene was not consumed according to monitoring by gas chromatography without the formation of diphenylmethylene(3-methylcyclopentadienyl)(9-fluorene) which is the ligand of diphenylmethylene(3-methylcyclopentadienyl)(fluorenyl)zirconium dichloride.

EXAMPLE 6
[Solution Polymerization of Ethylene/1-Hexene]

In a one-liter reactor were placed 600 mL of an aliphatic hydrocarbon (IP Solvent 1620, produced by Idemitsu Petrochemical Co.) as the solvent, and 20 mL of 1-hexene. The temperature of the reactor was set at 170° C. Thereto ethylene was fed to keep the pressure in the reactor at 20 kg/cm$^2$.

Separately in another vessel, 0.5 μmol of diphenylmethylene(3-methylcyclopentadienyl)(fluorenyl) zirconium dichloride was dissolved in toluene. Thereto, a solution of triisobutylaluminum in toluene (triisobutylaluminum concentration: 20% by weight) was added in an amount of 125 μmol in terms of aluminum. The mixture was stirred for one hour. Then this mixture was added to a solution of 0.6 μmol of N,N-dimethylanilinium tetrakis(pentafluorophenyl)borate in 1 mL of toluene, and the mixture was stirred for 10 minutes. The resulting by the mixture was introduced into the aforementioned reactor by application of nitrogen pressure.

After the introduction of the mixture, the temperature of the reactor was raised to 170° C., and the reactor was stirred at a rate of 1500 rpm for 20 minutes to allow the polymerization reaction to proceed. The obtained polymer was dried under vacuum at 100° C. for 6 hours. Thereby, 35.2 g of a copolymer was obtained. The MFR and other measured properties of the copolymer are shown in Table 1.

EXAMPLES 7–13

Solution polymerization of ethylene/1-hexene was conducted in the same manner as in Example 6 except that the polymerization conditions were changed as shown in Table 1. The results are shown also in Table 1.

COMPARATIVE EXAMPLE 2

The copolymerization was conducted in the same manner as in Example 1 except that diphenylmethylene- (cyclopentadienyl)(indenyl)zirconium dichloride was used in place of diphenylmethylene(3-methylcyclopentadienyl)(fluorenyl)zirconium dichloride, and the polymerization temperature was 150° C. The results are shown in Table 1.

minutes. Then this mixture was added to a solution of 0.28 µmol of N,N-dimethylanilinium tetrakis(pentafluorophenyl)borate in 1 mL of toluene, and the mixture was stirred for 10

TABLE 1

| | Transition metal compound µmol | Al compound µmol | Third Component µmol | Polymerization temperature ° C. | Polymer yield g | MFR (190° C.) g/10 min | Mw g/mol ×10$^4$ | Qw | Tm ° C. |
|---|---|---|---|---|---|---|---|---|---|
| Example | | | | | | | | | |
| 6 | Ph$_2$C(3-MeCp)(Flu)ZrCl$_2$ 0.5 | TIBAL 125 | PhMe$_2$NH.B(C$_6$F$_5$)$_4$ 0.6 | 170 | 35.2 | 6.5 | 6.1 | 2.0 | 119 |
| 7 | Ph$_2$C(3-MeCp)(Flu)ZrCl$_2$ 0.5 | TIBAL 125 | PhMe$_2$NH.B(C$_6$F$_5$)$_4$ 0.6 | 200 | 21.0 | 20.6 | | | 120 |
| 8 | Ph$_2$C(3-iPrCp)(Flu)ZrCl$_2$ 0.5 | TIBAL 125 | PhMe$_2$NH.B(C$_6$F$_5$)$_4$ 0.6 | 170 | 32.0 | 5.5 | 6.7 | 2.0 | 120 |
| 9 | Ph$_2$C(3-iPrCp)(Flu)ZrCl$_2$ 0.5 | TIBAL 125 | PhMe$_2$NH.B(C$_6$F$_5$)$_4$ 0.6 | 200 | 27.0 | 66.9 | 3.4 | 2.1 | 121 |
| 10 | Ph$_2$C(3,4-Me$_2$Cp)(Flu)ZrCl$_2$ 0.5 | TIBAL 125 | PhMe$_2$NH.B(C$_6$F$_5$)$_4$ 0.6 | 170 | 43.0 | 1.8 | 8.8 | 1.9 | 123 |
| 11 | Ph$_2$C(3,4-Me$_2$Cp)(Flu)ZrCl$_2$ 0.5 | TIBAL 125 | PhMe$_2$NH.B(C$_6$F$_5$)$_4$ 0.6 | 200 | 12.0 | 5.2 | | | 123 |
| 12 | Ph$_2$C(3,4-Me$_2$Cp)(Flu)ZrCl$_2$ 0.5 | TIBAL 125 | Ph$_3$C.B(C$_6$F$_5$)$_4$ 0.6 | 170 | 45.0 | 1.5 | | | 123 |
| 13 | Ph$_2$C(3,4-Me$_2$Cp)(Flu)ZrCl$_2$ 0.5 | MAO 1000 | — | 170 | 47.5 | 1.2 | | | 122 |
| Comparative Example | | | | | | | | | |
| 2 | Ph$_2$C(Cp)(Ind)ZrCl$_2$ 0.5 | TIBAL 125 | PhMe$_2$NH.B(C$_6$F$_5$)$_4$ 0.6 | 150 | 2.0 | 120 | | | |

Solvent: 600 mL, Ethylene: 20 kg/cm$^2$, 1-Hexene: 20 mL, Polymerization time: 20 minutes
Ph$_2$C(3-MeCp)(Flu)ZrCl$_2$: Diphenylmethylene(3-methylcyclopentadienyl)(fluorenyl)zirconium dichloride
Ph$_2$C(3-iPrCp)(Flu)ZrCl$_2$: Diphenylmethylene(3-isopropylcyclopentadienyl)(fluorenyl)Zirconium dichloride
Ph$_2$C(3,4-Me$_2$Cp)(Flu)ZrCl$_2$: Diphenylmethylene(3,4-dimethylcyclopentadienyl)(fluorenyl)zirconium dichloride
Ph$_2$C(Cp)(Ind)ZrCl$_2$: Diphenylmethylene(cyclopentadienyl)(indenyl)zirconium dichloride
TIBAL: Triisobutylaluminum,
MAO: Methylaluminoxane,
PhMe$_2$NH.B(C$_6$F$_5$)$_4$: N,N-dimethylanilinium tetrakis(pentafluorophenyl)borate,
Ph$_3$C.B(C$_6$F$_5$)$_4$: Trityl tetrakis(pentafluorophenyl)borate

EXAMPLE 14

[Slurry Polymerization of Ethylene/Hexene-1]

In a 2-liter reactor were placed 1000 mL of toluene as the solvent, 20 mL of 1-hexene, and a solution of triisobutylaluminum in toluene (triisobutylaluminum concentration: 20% by weight) in an amount of 440 µmol in terms o f aluminum, and the temperature of the reactor was set at 80° C. Thereto, ethylene was fed to keep the pressure in the reactor at 4 kg/cm$^2$.

Separately in another vessel, 0.23 µmol of diphenylmethylene (3-methylcyclopentadienyl) (fluorenyl)zirconium dichloride was dissolved in toluene. Thereto, a solution of triisobutylaluminum in toluene (triisobutylaluminum concentration: 20% by weight) was added in an amount of 58 µmol in terms of aluminum. The mixture was stirred for 10 minutes. The resulting mixture was introduced into the aforementioned reactor by the application of nitrogen pressure.

After the introduction of the mixture, the reactor was stirred at a rate of 600 rpm at 80° C. for 10 minutes to allow the polymerization reaction to proceed. The obtained polymer was dried under vacuum at 100° C. for 6 hours. Thereby 52.4 g of a copolymer was obtained. The MFR and other measured properties are shown in Table 2.

EXAMPLES 15–18

Slurry polymerization of ethylene/1-hexene was conducted in the same manner as in Example 14 except that the polymerization conditions were changed as shown in Table 2. The results are shown in Table 2.

TABLE 2

| Example | Transition metal Compound | µmol | Ethylene kg/cm$^2$ G | 1-Hexene mL | Polymerization temperature ° C. | Polymer yield g | MFR (190° C.) g/10 min | Tm ° C. |
|---|---|---|---|---|---|---|---|---|
| 14 | Ph$_2$C(3-MeCp)(Flu)ZrCl$_2$ | 0.23 | 4 | 20 | 80 | 52.4 | 0.06 | 105 |
| 15 | Ph$_2$C(3-iPrCp) (Flu)ZrCl$_2$ | 0.23 | 4 | 20 | 80 | 2.9 | 0.03 | 109 |
| 16 | Ph$_2$C(3,4-Me$_2$Cp)(Flu)ZrCl$_2$ | 0.23 | 4 | 20 | 80 | 3.9 | 0.02 | 112 |
| 17 | Ph$_2$C(3-PhCH$_2$Cp)(Flu)ZrCl$_2$ | 0.23 | 4 | 20 | 80 | 33.6 | 0.05 | 100 |
| 18 | Ph$_2$C(3-Me$_3$SiCp)(Flu)ZrCl$_2$ | 0.23 | 4 | 20 | 80 | 1.4 | 0.02 | 112 |

Transition metal compound/PhMe$_2$NH.B(C$_6$F$_5$)$_4$/Al(iBu)$_3$ = 1.0/1.2/2165
Toulene: 1000 mL, Polymerization time 10 minutes,
Ph$_2$C(3-MeCp)(Flu)ZrCl$_2$: Diphenylmethylene(3-methylcyclopentadienyl)(fluorenyl)zirconium dichloride
Ph$_2$C(3-iPrCp(Flu)ZrCl$_2$: Diphenylmethylene(3-isopropylcyclopentadienyl)(fluorenyl)zirconium dichloride

TABLE 2-continued

| Example | Transition metal Compound | μmol | Ethylene kg/cm² G | 1-Hexene mL | Polymerization temperature °C. | Polymer yield g | MFR (190° C.) g/10 min | Tm °C. |
|---|---|---|---|---|---|---|---|---|

Ph₂C(3,4-Me₂Cp)(Flu)ZrCl₂: Diphenylmethylene(3,4-dimethylcyclopentadienyl)(fluorenyl)zirconium dichloride
Ph₂C(3-PhCH₂Cp)(Flu)ZrCl₂: Diphenylmethylene(3-benzylcyclopentadienyl)(fluorenyl)zirconium dichloride
Ph₂C(3-Me₃SiCp)(Flu)ZrCl₂: Diphenylmethylene(3-(trimethylsilyl)cyclopentadienyl)(fluorenyl)zirconium dichloride

EXAMPLE 19
[Synthesis of Elastomer by Ethylene/1-Hexene Copolymerization]

In a 2-liter autoclave 850 mL of toluene and 150 mL of 1-hexene were mixed and heated with stirring to 40° C. The internal pressure was 0.2 kg/cm². Thereto, ethylene was introduced to keep the total pressure at 4.2 kg/cm². Separately, in another reactor, 10 mL of toluene, 0.6 μmol of N,N-dimethylanilinium tetrakis(pentafluorophenyl)borate, 500 μmol of triisobutylaluminum, and 0.5 μmol of diphenylmethylene (3-methylcyclopentadienyl) (fluorenyl) zirconium dichloride were mixed and stirred for 30 minutes. This mixed solution was introduced into the above autoclave to initiate polymerization. The polymerization was conducted by feeding ethylene to keep the total pressure at 4.2 kg/cm² at an internal temperature of 40° C. After 10 minutes, the polymerization was stopped by introducing 10 mL of ethanol into the autoclave.

The produced polymer was washed with a large amount of ethanol, and was dried at a reduced pressure at 90° C. for 8 hours. Thereby 18.0 g of ethylene/1-hexene copolymer was obtained. The copolymer contained 1-hexene units at a content of 21.0 mol %, and had an MFR of 0.30 g/10 min measured at 230° C. at a load of 2.16 kg/cm². The results are shown in Table 3.

EXAMPLE 20

Ethylene and 1-hexene were copolymerized in the same manner as in Example 19 except that the polymerization conditions were changed as shown in Table 3. The results are shown in Table 3.

COMPARATIVE EXAMPLE 3

The copolymerization was conducted in the same manner as in Example 19 except that bis(1,3-dimethylcyclopentadienyl)zirconium dichloride was used in place of diphenylmethylene(3-methylcyclopentadienyl)(fluorenyl)zirconium dichloride and the other polymerization conditions were as shown in Table 3. The results are shown in Table 3.

COMPARATIVE EXAMPLE 4

The copolymerization was conducted in the same manner as in Example 19 except that isopropylidene(cyclopentadienyl)(fluorenyl)zirconium dichloride was used in place of diphenylmethylene(3-methylcyclopentadienyl)(fluorenyl)zirconium dichloride and the other polymerization conditions were as shown in Table 3. The results are shown in Table 3.

TABLE 3

| | | Polymerization conditions | | | Polymerization results | | | |
|---|---|---|---|---|---|---|---|---|
| | Transition metal compound | μmol | 1-Hexene mL | Polymer Yield g | Hexene content mol % | MFR (230° C.) g/10 min | Tm °C. | |
| Example | | | | | | | | |
| 19 | Ph₂C(3-MeCp)(Flu)ZnCl₂ | 0.5 | 150 | 18.0 | 21.0 | 0.30 | None | |
| 20 | Ph₂C(3,4-Me₂Cp)(Flu)ZnCl₂ | 0.5 | 200 | 42.8 | 21.9 | 0.31 | None | |
| Comparative Example | | | | | | | | |
| 3 | (1,3-Me₂Cp)₂ZrCl₂ | 0.5 | 200 | 14.6 | 4.2 | * | 96 | |
| 4 | Me₂C(Cp)(Flu)ZrCl₂ | 5.0 | 200 | 0.6 | 32.0 | ** | None | |

Transition metal compound/PhMe₂NH.B(C₆F₅)₄/Al(iBu)₃ = 1.0/1.2/1000
Ethylene Partial pressure: 4.0 kg/cm²,
Toluene: 800 mL (Example 20 and Comparative Examples 3, 4), 850 mL (Example 19)
Polymerization temperature: 40° C.
Polymerization time: 10 min
*Not measurable because the polymer did not flow
**Not measureable because the molecular weight was low and the polymer was sticky
Ph₂C(3-MeCp)(Flu)ZnCl₂: Diphenylmethylene(3-methylcyclopentadienyl)(fluorenyl)zirconium dichloride
Ph₂C(3,4-Me₂Cp)(Flu)ZnCl₂: Diphenylmethylene(3,4-dimethylcyclopentadienyl)(fluorenyl)zirconium dichloride
(1,3-Me₂Cp)₂ZrCl₂: Bis(1,3-dimethylcyclopentadienyl)zirconium dichloride
Me₂C(Cp)(Flu)ZrCl₂: Isopropylidene(cyclopentadienyl)(fluorenyl)zirconium dichloride

EXAMPLE 21
[Slurry Polymerization of Propylene]

In a 2-liter reactor were placed 500 mL of toluene as the solvent, and 500 mL of propylene. The temperature of the reactor was set at 40° C.

Separately in another vessel, 4.6 μmol of diphenylmethylene(3-methylcyclopentadienyl)(fluorenyl)zirconium dichloride was dissolved in toluene. Thereto, a solution of triisobutylaluminum in toluene (triisobutylaluminum concentration: 20% by weight) was added in an amount of 1.2 mmol in terms of aluminum. The mixture was stirred for 10 minutes. Then this mixture was added to a solution of 5.5 µmol of N,N-dimethylanilinium tetrakis-(pentafluorophenyl)borate in 10 mL of toluene, and the mixture was stirred for 10 minutes. The resulting mixture was introduced into the aforementioned reactor by the application of nitrogen pressure.

After the introduction of the mixture, the content of the reactor was stirred at a rate of 600 rpm at 40° C. for 60 minutes to allow the polymerization reaction to proceed. The obtained polymer was dried under vacuum at 100° C. for 6 hours. Thereby, 43.0 g of a copolymer was obtained. The MFR and other measured properties of the polymer are shown in Table 4.

EXAMPLES 22–25

Propylene was polymerized in the same manner as in Example 21 except that the polymerization conditions were changed as shown in Table 4. The results are shown in Table 4.

COMPARATIVE EXAMPLE 5

The polymerization was conducted in the same manner as in Example 21 except that 5.0 µmol of isopropylidene-(cyclopentadienyl)(fluorenyl)zirconium dichloride was used in place of diphenylmethylene(3-methylcyclopentadienyl)-(fluorenyl) zirconium dichloride, the amount of triisobutylaluminum was changed to 500 µmol, and the amount of N,N-dimethylanilinium tetrakis(pentafluorophenyl)borate was changed to 15 µmol. The results are shown in Table 4.

COMPARATIVE EXAMPLE 6

The polymerization was conducted in the same manner as in Example 21 except that 1.0 µmol of ethylenebis(indenyl)-zirconium dichloride was used in place of diphenylmethylene-(3-methylcyclopentadienyl)(fluorenyl) zirconium dichloride, the amount of triisobutylaluminum was changed to 500 µmol, and the amount of N,N-dimethylanilinium tetrakis-(pentafluorophenyl)borate was changed to 5 µmol. The results are shown in Table 4.

TABLE 4

| | Catalyst | | | | Polymerization results | | | | |
|---|---|---|---|---|---|---|---|---|---|
| | Transition metal compound | µmol | $PhMe_2NH.$ $B(C_6F_5)_4$ µmol | TIBAL µmol | Polymer yield g | MFR (190° C.) g/10 min | Mw g/mol ×10$^4$ | Qw | Tm ° C. |
| Example | | | | | | | | | |
| 21 | $Ph_2C(3\text{-}MeCp)(Flu)ZrCl_2$ | 4.6 | 5.5 | 1200 | 43.0 | 0.67 | 30.6 | 2.6 | 135 |
| 22 | $Ph_2C(3\text{-}iPrCp)(Flu)ZrCl_2$ | 4.6 | 5.5 | 1200 | 35.7 | 0.73 | 26.7 | 2.4 | 135 |
| 23 | $Ph_2C(3,4\text{-}Me_2Cp)(Flu)ZrCl_2$ | 4.6 | 5.5 | 1200 | 190 | 1.08 | 21.3 | 1.9 | — |
| 24 | $Ph_2C(3\text{-}PhCH_2Cp)(Flu)ZrCl_2$ | 4.6 | 5.5 | 1200 | 15.2 | 0.01 | | | 129 |
| 25 | $Ph_2C(3\text{-}Me_3SiCp)(Flu)ZrCl_2$ | 4.6 | 5.5 | 1200 | 39.5 | 0.68 | | | 114, 136 |
| Comparative Example | | | | | | | | | |
| 5 | $Me_2C(Cp)(Flu)ZrCl_2$ | 5.0 | 15 | 500 | 41.0 | | 8.0 | 2.5 | 126, 137 |
| 6 | $Et(Ind)_2ZrCl_2$ | 1.0 | 5 | 500 | 230 | 4.0 | 2.3 | | 141 |

Toluene: 500 mL, Propylene: 500 mL, Polymerization temperature: 40° C., Polymerization time: 60 minutes, Polymerization pressure: 10 kg/cm$^2$
$Ph_2C(3\text{-}MeCp)(Flu)ZrCl_2$: Diphenylmethylene(3-methylcyclopentadienyl)(fluorenyl)zirconium dichloride
$Ph_2C(3\text{-}iPrCp)(Flu)ZrCl_2$: Diphenylmethylene(3-isopropylcyclopentadienyl)(fluorenyl)zirconium dichloride
$Ph_2C(3,4\text{-}Me_2Cp)(Flu)ZrCl_2$: Diphenylmethylene(3,4-dimethylcyclopentadienyl)(fluorenyl)zirconium dichloride
$Ph_2C(3\text{-}PhCH_2Cp)(Flu)ZrCl_2$: Diphenylmethylene(3-benzylcyclopentadienyl)(fluorenyl)zirconium dichloride
$Ph_2C(3\text{-}Me_3SiCp)(Flu)ZrCl_2$: Diphenylmethylene(3-(trimethylsilyl)cyclopentadienyl)(fluorenyl)zirconium dichloride
$Me_2C(Cp)(Flu)ZrCl_2$: Isopropylidene(cyclopentadienyl)(fluorenyl)zirconium dichloride
$Et(Ind)_2ZrCl_2$: Ethylenebis(indenyl)zirconium dichloride
$PhMe_2NH.B(C_6F_5)_4$: N,N-dimethylanilinium tetrakis(pentafluorophenyl)borate
TIBAL: Triisobutylaluminum

EXAMPLE 26

[Preparation of Modified Clay A]

In a 2-liter flask 5.0 g of high-purity montmorillonite (Kunipia, trade name, Kunimine Kogyo K.K.) was dispersed in one liter of well-deaerated water. Thereto, an aqueous solution of 1.9 g (12.1 mmol) of N,N-dimethylaniline hydrochloride in 150 mL of water was added, and the mixture was stirred for 24 hours. Then the solid matter was collected from the mixture by filtration, washed with water and ethanol, and dried at room temperature under a reduced pressure to obtain modified clay A.

[Preparation of Liquid Catalyst Suspension]

In a 300 mL Schlenk vessel, 1.0 g of the above modified clay A was suspended in 56 mL of toluene. Thereto, 2.8 mL of a triethylaluminum solution (concentration: 1.44 mol/L in toluene) was added, and the mixture was stirred for one hour. Separately in a 50-mL Schlenk vessel, 39.5 mg (67.5 µmol) of diphenylmethylene(3,4-dimethylcyclopentadienyl) (fluorenyl)-zirconium dichloride, 40 mL of toluene, and 9.4 mL of triethylaluminum solution (concentration: 1.44 mmol/L in toluene) were mixed to obtain a solution. 29.2 mL of this solution was added to the aforementioned modified clay, and the mixture was stirred for 12 hours to obtain a catalyst suspension liquid.

[Solution Polymerization]

In a one-liter autoclave purged by nitrogen were placed 600 mL of a $C_9$–$C_{13}$ saturated hydrocarbon solvent (IP solvent, produced by Idemitsu Petrochemical Co.), and 20 mL of 1-hexene. Ethylene was fed to the autoclave to keep the internal pressure at 21 kg/cm$^2$, and the temperature was adjusted to 170° C. Thereto, 12 mL of decane containing 1.1 mL of the catalyst suspension liquid (0.5 µmol in terms of zirconium) prepared above was added, and polymerization was allowed to proceed. After polymerization for 10 minutes, the unreacted ethylene was removed, and the reaction solution was poured into ethanol to obtain 51 g of polymer. The results are shown in Table 5.

EXAMPLES 27–29

Solution polymerization of ethylene/1-hexene was conducted in the same manner as in Example 1 except that the polymerization conditions were changed as shown in Table 5. The results are shown in Table 5

EXAMPLE 30

[Preparation of Modified Clay Compound B]

A modified clay B was prepared in the same manner as in Example 26 except that synthetic hectorite (Laponite, trade name, Nippon Silica Co.) was used in place of the high-purity montmorillonite. [Preparation of Catalyst Suspension Liquid and Solution Polymerization]

The preparation of the catalyst suspension liquid and the solution polymerization were conducted in the same manner as in Example 26 except that the modified clay B was used in place of the modified clay A. The results are shown in Table 5.

EXAMPLE 31

The solution polymerization was conducted in the same manner as in Example 30 except that diphenylmethylene-(3-isopropylcyclopentadienyl)(fluorenyl)zirconium dichloride was used in place of diphenylmethylene(3,4-dimethylcyclopentadienyl)(fluorenyl)zirconium dichloride. The results are shown in Table 5.

TABLE 5

| Example | Transition metal compound μmol | Al compound μmol | Modified clay compound mg | Polymerization temperature °C. | Polymer yield g | MFR (190° C.) g/10 min |
|---|---|---|---|---|---|---|
| 26 | Ph$_2$C(3,4-Me$_2$Cp)(Flu)ZrCl$_2$ 0.5 | TIBAL 125 | Modified clay A 12.5 | 170 | 51 | 6.0 |
| 27 | Ph$_2$C(3-Me$_3$SiCp)(Flu)ZrCl$_2$ 0.5 | TIBAL 125 | Modified clay A 12.5 | 170 | 25 | 3.7 |
| 28 | Ph$_2$C(3-PhCH$_2$Cp)(Flu)ZrCl$_2$ 0.5 | TIBAL 125 | Modified clay A 12.5 | 170 | 16 | 2.0 |
| 29 | Ph$_2$C(3-iPrCp)(Flu)ZrCl$_2$ 0.5 | TIBAL 125 | Modified clay A 12.5 | 170 | 60 | 23.6 |
| 30 | Ph$_2$C(3,4-Me$_2$Cp)(Flu)ZrCl$_2$ 0.5 | TIBAL 125 | Modified clay B 12.5 | 170 | 63 | 7.3 |
| 31 | Ph$_2$C(3-iPrCp)(Flu)ZrCl$_2$ 0.5 | TIBAL 125 | Modified clay B 12.5 | 170 | 71 | 18.5 |

Solvent: 600 mL, Ethylene 20 kg/cm$^2$, 1-Hexene: 20 mL, Polymerization time: 10 minutes,
Ph$_2$C(3,4-Me$_2$Cp)(Flu)ZrCl$_2$: Diphenylmethylene(3,4-dimethylcyclopentadienyl)(fluorenyl)zirconium dichloride
Ph$_2$C(3-Me$_3$SiCp)(Flu)ZrCl$_2$: Diphenylmethylene(3-(trimethylsilyl)cyclopentadienyl)(fluorenyl)zirconium dichloride
Ph$_2$C(3-PhCH$_2$Cp)(Flu)ZrCl$_2$: Diphenylmethylene(3-benzylcyclopentadienyl)(fluorenyl)zirconium dichloride
Ph$_2$C(3-iPrCp)(Flu)ZrCl$_2$: Diphenylmethylene(3-isopropylcyclopentadienyl)(fluorenyl)zirconium dichloride
TIBAL: Triisobutylaluminum,
Modified clay A: N,N-dimethylanilinium-modified montmorillonite
Modified clay B: N,N-dimethylanilinium-modified hectorite The present invention provides a transition metal compound having a substituted cyclopentadienyl group as a ligand and a fluorenyl group as another ligand, both ligands being bridged by a diarylmethylene group. By use of this transition metal compound as the catalyst component, a polyolefin having a high molecular weight can be produced with high productivity.

What is claimed is:

1. A process for producing an olefin polymer comprising polymerizing using a polymerization catalyst comprising:
   (a) a transition metal compound represented by formula (1);
   (b) a compound capable of a reacting with the transition metal compound to form a cationic transition metal compound; and
   (c) an organometallic compound;
   where the transition metal compound represented by formula (1) is:

(1)

where $M^1$ is a transition metal of Group 4 of the Periodic Table; wherein $R^{13}$ is independently a hydrogen atom, an alkyl group, an alkenyl group, an aryl group or an arylalkyl group, each of which may have 1–20 carbons; $R^2$ is independently a hydrogen atom or a hydrocarbon group of 1 to 20 carbons; $R^3$ and $R^4$ are hydrogen atoms; $R^5$ and $R^6$ are independently an aryl group of 6 to 10 carbons; $R^7$ and $R^8$ are respectively a substituent of the benzo ring of the fluorenyl group, and are independently a hydrocarbon group of 1 to 20 carbons; $Q^1$ and $Q^2$ are independently a hydrogen atom, a halogen atom or a hydrocarbon group of 1 to 20 carbons; and m and n are independently an integer of 0 to 4;
wherein the compound (b) is selected from the group consisting of compounds of the following formulae (6) and (7) and a clay mineral:

$$(HL^1{}_l)(M^3R^{10}{}_4) \tag{6}$$

wherein H is proton, each $L^1$ is independently a Lewis base 1 satisfies, 0<1<2, $M^3$ is a boron, aluminum, or gallium atom, and each $R^{10}$ is independently a halogen-substituted aryl group of 6 to 20 carbons;

$$(C)(M^3R^{10}_4) \tag{7}$$

wherein C is a carbonium cation or tropylium cation, $M^3$ is a boron, aluminum, or gallium atom, and each $R^{10}$ is independently a halogen-substituted aryl group of 6 to 20 carbons;

where the clay mineral used in the present invention is preliminarily subjected to a chemical treatment, where the chemical treatment is a chemical treatment which includes an acid or alkali treatment, a salt treatment or complex formation by treatment with an organic or inorganic compound wherein the organometallic compound (c) is represented by formula (13):

$$M^5R^{12}_s$$

wherein $M^5$ is aluminum and each $R^{12}$ is independently an alkyl group of 1 to 24 carbons; and s is 3.

2. The process according to claim 1, wherein the polymerizing is performed at a temperature not lower than 120° C.

3. The process according to claim 1, wherein $R^2$ in formula (1) is the alkyl group having 1–20 carbon atoms and wherein the polymerizing is performed at a temperature not lower than 120° C.

4. The process according to claim 1, wherein $Q_1$ and $Q_2$ are independently halogen atoms.

* * * * *